United States Patent [19]

Bahrmann et al.

[11] Patent Number: 5,382,716
[45] Date of Patent: Jan. 17, 1995

[54] DECYL ALCOHOL MIXTURES, PHTHALIC OBTAINABLE THEREFROM, AND THEIR USE AS PLASTICIZERS

[75] Inventors: Helmut Bahrmann, Hamminkeln; Wolfgang Greb, Dinsklaken; Peter Heymanns, Essen; Peter Lappe, Dinslaken; Jürgen Szameitat, Wesel; Thomas Müller, Dinslaken; Ernst Wiebus, Oberhausen, all of Germany

[73] Assignee: Hoechst Aktiengesellschaft, Germany

[21] Appl. No.: 36,026

[22] Filed: Mar. 23, 1993

[30] Foreign Application Priority Data

Mar. 27, 1992 [DE] Germany ............... 4210028

[51] Int. Cl.$^6$ ............................................. C07C 29/16
[52] U.S. Cl. ..................... 568/883; 568/454; 568/463; 568/840; 568/850; 568/881; 568/882
[58] Field of Search ............. 568/881, 882, 883, 463, 568/454, 850, 840

[56] References Cited

U.S. PATENT DOCUMENTS 4,658,068  4/1987  Hanin ............................ 568/451

FOREIGN PATENT DOCUMENTS 0052999   6/1982  European Pat. Off. ........... 568/882
0094456  11/1983  European Pat. Off. ........... 568/883
3227534   9/1983  Japan ............................ 568/883
116092    6/1989  Japan ............................ 568/883

*Primary Examiner*—Werren B. Lone
*Attorney, Agent, or Firm*—Jordan B. Bierman

[57] ABSTRACT

Mixtures of isomeric decyl alcohols obtained by hydroformylation of butadiene to produce aldehyde mixtures, condensation of the aldehyde mixtures, isolated from the reaction product, to form an aldol mixture, and isolation and hydrogenation of the aldol mixture. The mixture of isomeric decyl alcohols, esterified using phthalic acid, gives a mixture of isomeric decyl phthalates which are plasticizers having excellent cold properties.

11 Claims, No Drawings

DECYL ALCOHOL MIXTURES, PHTHALIC OBTAINABLE THEREFROM, AND THEIR USE AS PLASTICIZERS

This Application claims the benefit of the priority of German Application P 42 10 028.3, filed Mar. 27, 1992.

The invention relates to mixtures of isomeric decyl alcohols, a process for the preparation thereof, the phthalic esters obtained from these alcohols, and use of the esters as plasticizers.

BACKGROUND OF THE INVENTION

Esters of phthalic acid are used to a great extent as plasticizers, in particular for polyvinyl chloride. The principal alcohol components are primary alcohols having 8 to 10 carbon atoms; the most important of these is currently 2-ethylhexanol. Although phthalic esters of short-chain alcohols lead to plasticizers having good gelling capacity, their higher volatility is disadvantageous. Longer chain esters, on the other hand, gel more slowly and have a poorer cold resistance.

The properties of the phthalic ester plasticizers are influenced, not only by the size of the alcohol molecule, but also by the branching of the carbon chain. Thus, alcohols having little branching give ester plasticizers having high cold flexibility; substantially linear alcohols having 8 to 10 carbon atoms in the molecule are thus increasing in importance as the alcohol component. A precondition for their use is that they are available in large amounts and at favorable cost.

According to German Patent 28 55 421, phthalates of nine-carbon alcohols are used as plasticizers and are obtained by oxo reaction of eight carbon olefins, hydrogenation of the reaction product, and esterification of the resultant nine-carbon alcohols with phthalic anhydride. 3% to 20% by weight of the starting olefins have an isobutane skeleton in each molecule chain, less than 3% by weight of the olefins have quaternary carbon, and more than 90% by weight of the total amount of the olefins are present as n-octenes, monomethylheptenes, and dimethylhexenes. In addition, the weight ratio of the total amount of the n-octenes and monomethylheptenes to the dimethylhexenes is more than 0.8.

Phthalic esters based on ten-carbon alcohols are an object of European Patent Application 366,089. These alcohols are used in the form of a mixture which is obtained by hydroformylation of a butene fraction, aldol condensation of the resulting aldehyde mixture, and subsequent hydrogenation.

Another route to obtain a didecyl phthalate mixture is described in European Patent Application 424,767. The preparation of the esters is carried out in a multi-stage process by dimerization of butene mixtures, hydroformylation and hydrogenation of the resulting octene mixture to give a nonanol mixture dehydration of the nonanol mixture to a nonene mixture, and hydroformylation and hydrogenation of the nonene mixture, thereby to form a decanol mixture.

The known processes do not fulfill all the economic and technical requirements of a process carried out on an industrial scale, because the starting materials are not available in sufficient quantity and/or are not available at favorable costs, and/or the conversion of the starting materials into the alcohols is associated with processes which are too expensive.

SUMMARY OF THE INVENTION

The object was therefore to develop a process which starts from raw materials which are cheaply available and which can also be converted in an industrially simple manner into the desired alcohols.

The invention comprises mixtures of isomeric decyl alcohols, obtained by hydroformylation of butadiene to give an aldehyde mixture, isolation of the resulting aldehyde mixture from the reaction product, condensation of the aldehyde mixture to form an aldol mixture, and isolation and hydrogenation of the aldol mixture to the desired mixture of isomeric decyl alcohols.

The butadiene starting material is not only easily obtained by dehydrogenation of butane or butene, but is also unavoidably produced in substantial quantities in the preparation of ethylene by thermal cracking of light petroleum or higher hydrocarbons. It is isolated from the four-carbon cracking cuts of the pyrolysis product; for example, by liquid-liquid extraction using a selective solvent such as acetonitrile, dimethylformamide or N-methylpyrrolidone.

Butadiene is used for the hydroformylation in its usual commercial form, i.e. a purity of at least 99.5% by weight. The hydroformylation of the conjugated diolefin is a reaction known per se. It proceeds under the action of both cobalt catalysts and rhodium catalysts; the cobalt-catalyst reaction is described, for example, by Adkins and Williams (J. Org. Chem. 17, 980, (1952)). A mixture of n- and i-valeraldehydes in a molar ratio of 1:1 is formed in moderate yield.

Considerably more favorable aldehyde yields are achieved when the hydroformylation of butadiene is carried out in the presence of rhodium catalysts. Complex compounds of rhodium with a multidentate ligand which contains trivalent phosphorous atoms have proven themselves. A process based on such catalysts is described, or example, in European Patent 33 554.

In the context of the present invention, preference is given to the hydroformylation of the butadiene in a heterogeneous two-phase system. It is described, for example, in German Patent 26 27 354. Such a process is distinguished by the presence of an organic phase, which contains the starting olefin and the reaction product, and an aqueous phase, in which the catalyst is dissolved. Catalysts used are water-soluble rhodium complexes with water-soluble phosphines as ligands. The water-soluble phosphines include, in particular, triarylphosphines, trialkylphosphines and alkyl-, aryl- or alkylaryldiphosphines. The organic radicals of the phosphines are substituted by sulfonic acid groups or carboxyl groups. Their preparation is taught, for example, in German Patent 26 27 354 and German Democratic Republic Patent 259 194. The reaction is carried out at temperatures of 60° to 150° C., preferably 90° to 120° C., and at pressures from 0.4 to 30, in particular 1 to 10, MPa. The rhodium concentration is 20 to 2000 ppm by weight, preferably 50 to 500 ppm by weight, based on the aqueous catalyst solution; 4 to 100 mol of water-soluble phosphine are used per mol of rhodium. The volume ratio of aqueous to organic phase is 0.1 to 10:1.

The butadiene conversion is markedly increased if a phase transfer reagent (solubilizer) is added to the aqueous catalyst solution. Proven cationic solubilizers are of the formula $[A-N(R^1R^2R^3)]^+E^-$ in which A is a straight or branched chain alkyl radical having 6 to 25 carbon atoms, $R^1$, $R^2$, $R^3$ are independently straight or branched chain alkyl radicals having 1 to 4 carbon atoms, and E may be sulfate, tetrafluoroborate, acetate, methosulfate, benzenesulfonate, alkylbenzenesulfonate, toluenesulfonate, lactate, or citrate.

The hydroformylation of butadiene using rhodium as the catalyst produces, both in the single-phase and in the two-phase reaction systems, a mixture of predominantly saturated aldehydes in high yield. The ratio of saturated to unsaturated aldehydes can be varied within broad limits by variation of the hydrogen component in the synthesis gas. Increased hydrogen partial pressure favors the formation of saturated aldehydes.

The aldehyde mixture contains 90% or more of n-valeraldehyde and, in lesser amounts, other aldehydes, including i-valeraldehyde, dialdehydes, and other by-products. The composition of the aldehyde mixture can be varied by selection of the phosphine ligands. Particularly high n/i ratios are attained using water-soluble rhodium catalysts which contain water-soluble alkylphosphines or alkyl- or aryldiphosphines as ligands.

After the hydroformylation is completed, the aldehyde mixture is isolated from the catalyst, from the unreacted reactants, and from the other reaction products. When the reaction takes place in homogeneous phase, distillation is the conventional separation process. If the hydroformylation was carried out in a two-phase system, product and catalyst can be separated from each other by a simple phase separation. In industrial implementation, this process is considerably simpler and, because of the absent thermal stress, is also considerably gentler than the isolation of the aldehyde mixture by distillation. The hydroformylation of the butadiene can be carried out discontinuously or continuously, independently of the process used. A high selectivity to give n-valeraldehyde is achieved if only part of the butadiene used is converted into aldehyde and the remainder is recycled.

The aldol condensation of the aldehydes present as a mixture is carried out in the conventional manner in the presence of basic catalysts. A pretreatment of the aldehydes, for example special purification, is not required. The catalysts used are alkali metal carbonates or alkali metal hydroxides, in particular compounds of sodium or potassium and amines, preferably tertiary amines, such as triethylamine, tri-n-propylamine, and tri-n-butylamine. Temperatures of 60° to 160° C., in particular 80° to 130° C., are employed, and atmospheric pressure or elevated pressure up to about 1 MPa is also used. The reaction time is a few minutes to several hours and is dependent, in particular, on the type of catalyst and reaction temperature. Because of its higher reaction rate, n-valeraldehyde principally dimerizes with itself or with isomeric valeraldehydes to give decenals; in contrast, condensation of the branched give carbon aldehydes among themselves does not occur.

The aldehyde mixture obtained by condensation is then hydrogenated to give a decyl alcohol mixture. The hydrogen addition takes place in a known manner in the presence of catalysts. Suitable catalysts are, for example, hydrogenation catalysts based on nickel, chromium, or copper. The hydrogenation temperature is conventionally between 100° and 180° C. and the pressure between 1 and 10 MPa. The decyl alcohol mixture is distilled for purification.

The mixture is especially suitable as the alcohol component of phthalic esters which are used as plasticizers. The preparation of the phthalic esters is known [Ullmann, Encyclopädie der Technischen Chemie (Encyclopedia of Industrial Chemistry) (1979), volume 18, pp 536 ff]. Phthalic anhydride is expediently reacted with the decyl alcohol mixture in the molar ratio 1:2 in a single stage. The reaction rate can be increased by catalysts and/or by increasing the reaction temperature. In order to displace the equilibrium in the direction of ester formation, it is necessary to eliminate the water formed from the reaction mixture.

The phthalates obtained from the decyl alcohol mixture according to the invention are plasticizers having excellent cold properties.

What we claim is:

1. A mixture of isomeric decyl alcohols which is the product of hydroformylation of butadiene to form a reaction product containing an aldehyde mixture, separating said aldehyde mixture from said reaction product, condensation of said aldehyde mixture, thereby forming a condensation product containing an aldol mixture, separating said aldol mixture from said condensation product, and hydrogenation of said aldol mixture to said mixture of isomeric decyl alcohols.

2. The mixture of claim 1 wherein said hydroformylation is carried out in the presence of at least one rhodium catalyst.

3. The mixture of claim 2 wherein said catalyst is a water soluble rhodium-phosphine complex and said hydroformylation is carried out in the presence of water, said complex being in an aqueous catalyst solution.

4. The mixture of claim 3 wherein said phosphine is sulfonated.

5. The mixture of claim 4 wherein said complex contains sulfonated alkyl- or arylphosphines.

6. The mixture of claim 4 wherein said complex contains sulfonated aryl, alkyl-, or arylalkyldiphosphines.

7. The mixture of claim 3 wherein said hydroformylation is carried out at a reaction temperature of 70° to 150° C. and under a reaction pressure of 0.4 to 30 MPa, there being an aqueous phase and an organic phase in a volume ratio of 0.1 to 10:1, said rhodium being in said aqueous catalyst solution in an amount of 20 to 2000 ppm based on said catalyst solution, and there being 4 to 100 mols of said phosphine per mol of said rhodium.

8. The mixture of claim 3 wherein a phase transfer agent is in said aqueous catalyst solution.

9. The mixture of claim 8 wherein said transfer agent is of the formula $[A—N(R^1R^2R^3)]^{30} E^-$, wherein A is a straight or branched chain alkyl radical having 6 to 25 carbon atoms, $R^1$, $R^2$, and $R^3$ are independently straight or branched chain alkyl radicals having 1 to 4 carbon atoms, and E is selected from the group consisting of sulfate, tetrafluoroborate, acetate, methosulfate, benzene sulfonate, alkylbenzosulfonate, toluenesulfonate, lactate, and citrate.

10. The mixture of isomeric didecal phthalates which is the reaction product of esterification of phthalic acid or phthalic anhydride with the mixture of isomeric decyl alcohols of claim 1.

11. Use of the mixture of isomeric didecyl phthalates of claim 10 as plasticizer.

* * * * *